(12) United States Patent
Jelovac et al.

(10) Patent No.: US 9,259,300 B2
(45) Date of Patent: Feb. 16, 2016

(54) DEVICE FOR DISPENSING A DENTAL MATERIAL

(75) Inventors: Emir Jelovac, Munich (DE); Marc Peuker, Schondorf (DE); Ozcan Donmez, Landsberg am Lech (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 100 days.

(21) Appl. No.: 13/808,968

(22) PCT Filed: Jul. 15, 2011

(86) PCT No.: PCT/US2011/044133
§ 371 (c)(1),
(2), (4) Date: Jan. 8, 2013

(87) PCT Pub. No.: WO2012/009610
PCT Pub. Date: Jan. 19, 2012

(65) Prior Publication Data
US 2013/0115568 A1    May 9, 2013

(30) Foreign Application Priority Data

Jul. 16, 2010   (EP) ..................................... 10169763

(51) Int. Cl.
*A61C 9/00* (2006.01)
*A61C 5/06* (2006.01)
*B05C 17/01* (2006.01)

(52) U.S. Cl.
CPC ............... *A61C 9/0026* (2013.01); *A61C 5/064* (2013.01); *B05C 17/0133* (2013.01)

(58) Field of Classification Search
CPC .................. A61C 5/06–5/068; A61C 9/0026; B05C 17/0133
USPC ........ 433/36, 80–90; 222/135, 137, 325–327; 604/224
See application file for complete search history.

(56) References Cited

U.S. PATENT DOCUMENTS

| 6,168,052 | B1 | 1/2001 | Keller | |
|---|---|---|---|---|
| 7,361,161 | B2 | 4/2008 | Bainton | |
| 2005/0048437 | A1* | 3/2005 | Kamohara et al. | 433/89 |
| 2007/0023456 | A1* | 2/2007 | Jalali et al. | 222/391 |
| 2008/0177236 | A1* | 7/2008 | Burren et al. | 604/224 |

FOREIGN PATENT DOCUMENTS

| DE | 203 17 377 | 4/2005 |
|---|---|---|
| EP | 1 700 639 | 9/2006 |

(Continued)

OTHER PUBLICATIONS

International Search Report for International Publication No. PCT/US2011/044133, dated Aug. 29, 2011.

(Continued)

*Primary Examiner* — Edward Moran

(57) ABSTRACT

A device for dispensing a dental material comprises a compartment for the dental material, a piston for extruding the dental material from the compartment, and a spindle drive for moving the piston and the compartment relative to one another. The spindle drive comprises first and second threads which are operable for moving the piston. The first thread has a first pitch and the second thread has a different second pitch. In one embodiment, the invention may provide a relatively inexpensive and reliable dental dispensing device.

4 Claims, 6 Drawing Sheets

(56) References Cited

FOREIGN PATENT DOCUMENTS

| EP | 2 407 250 | 1/2012 |
|---|---|---|
| WO | 03/075985 | 9/2003 |
| WO | WO 2006/058883 | 6/2006 |
| WO | WO 2006/079481 | 8/2006 |
| WO | WO 2006/114010 | 11/2006 |
| WO | WO 2010/053569 | 5/2010 |
| WO | WO 2010/072229 | 7/2010 |
| WO | WO 2012/009610 | 1/2012 |

OTHER PUBLICATIONS

Extended European Search Report for Application No. 10169763.9, dated Jan. 28, 2011.

* cited by examiner

DEVICE FOR DISPENSING A DENTAL MATERIAL

CROSS REFERENCE TO RELATED APPLICATIONS

This application is a national stage filing under 35 U.S.C. 371 of International Application No. PCT/US2011/044133, filed Jul. 15, 2011, which claims priority to European Application No. 10169763.9, filed Jul. 16, 2010. The disclosures of both applications are incorporated by reference in their entirety herein.

FIELD OF THE INVENTION

The invention relates to a device for dispensing a dental material, and in particular to a device which has a spindle drive. The spindle drive comprises two threads having different pitches for causing a piston of the device to move.

BACKGROUND ART

In dentistry a variety of devices are available which allow for preparation and/or application of dental materials in a dentist's practice. In particular for preparation of materials that are typically used at larger amounts, like for example dental impression materials, devices have been developed that provide for automatic dispensing from packages and/or for mixing of such materials. An exemplary device for mixing and dispensing a dental impression material is for example available under the designation 3M™ ESPE™ Pentamix™ from 3M ESPE AG, Germany. Typically such a device allows for two material components to be simultaneously supplied from a package through a mixer where they are mixed. Often the devices provide for continuously extruding the components through a mixer, where the components are mixed as the components flow through the mixer and released from an outlet.

The devices further typically have a motor driven piston for extruding the material from a container. A variety of different drive concepts have been proposed for driving the piston at a relatively high force as it may be required for appropriately dispensing the dental material.

For example EP 1 700 639 discloses a device for dispensing a flowable substance. The device comprises at least one force transmitting member (for example a push-pull chain) adapted to transmit a pushing force in a direction toward or opposite the substance and which can be gathered non-linearly.

U.S. Pat. No. 6,168,052 discloses an electrically driven dispensing appliance having an electric drive which acts via drive screws on thrust plates for dispensing material from cartridges. The drive screws are axially stationary and are in action relationship with a slide bearing said thrust plates. The electric drive comprises a first gear motor for a drive under high load during advance and relief, and a second motor for the drive under lower load during the retracting and fast advance motions.

Although there is a variety of devices on the market which provide for automatic mixing and dispensing there is still a desire to minimize costs for manufacturing of such devices and for providing the devices with maximized reliability.

SUMMARY OF THE INVENTION

The invention relates to a device for dispensing a dental material. The device comprises at least one compartment for receiving the dental material, at least one piston for extruding the dental material from the compartment and a spindle drive for moving the piston and the compartment relative to one another. The spindle drive comprises a first thread and a second thread which are operable for moving the piston. Further the first thread has a first pitch and the second thread has a different second pitch.

The invention may be advantageous in that it allows a relatively simple and compact design of the device. In particular complex gear boxes may not be required. A design which is enabled by the invention may further help maximizing the use of standardized components as they may be available in the industry. For example a standard motor providing a standard rotation speed of for example 1500 rounds per minute or 3000 rounds per minute may be used in the device in combination with a transmission having no or only a few gears (for example only two or three gears). Further the invention may allow the use of threads that provide sufficient mechanical stability for extruding even high viscosity dental material. In particular fine pitches (typically resulting in a relatively low mechanical stability of a thread and thus in a relatively low force available for extruding material) may be avoided. The invention may further be advantageous in that it may enable relatively slow or extremely slow extrusion speeds of the material. This may allow the dispensation of relatively high viscous materials for example. The invention may further allow the use of relatively small and/or inexpensive motors.

In a preferred embodiment the device is adapted for receiving the dental material in the form of two material components. Such a device further preferably comprises at least one cartridge which contains the components of the dental material. The cartridge may have two individual compartments for containing the individual components of the dental material. The cartridge may for example be adapted for receiving a foil bag in each compartment, and each foil bag may contain a component of the dental material. A cartridge of another example may be adapted to directly contain a component in each compartment, and may comprise a plug for closing each compartment. Each plug may be adapted such that it seals with an inner wall of the compartment and such that it is movable in the compartment for extruding the component from the compartment. The device may have two pistons each being adapted to be moved into one of the compartments of the cartridge. The pistons may for example be adapted such that they can be moved into the compartments for compressing the foil bags and/or for advancing the plugs. Thus the pistons may cause the components to be extruded from the cartridge. The device may have at least one spindle drive for driving the two pistons, or two spindle drives each driving one piston. A spindle drive for each piston may allow a relative synchronous extrusion of the components because the spindle drives and the pistons may be arranged generally coaxially with one another and aligned with the direction of force used for extruding the components. Thus tilting of the pistons relative to each other may be prevented. The device may further comprise a mixer for mixing the components. Further the device may have a mixer shaft for receiving and driving the mixer. The mixer shaft may for example have a coupling for engaging with a coupling of the mixer. Therefore the mixer may be removably engaged with the mixer shaft. The mixer further may have two inlets each being adapted for connecting with an outlet of the cartridge. The outlets may be provided by the cartridge itself or at a part which is separable from the cartridge. For example the foil bags may comprise caps connected thereto. The caps may be receivable at and end of the cartridge and may provide an outlet for the foil bags.

Further the compartments may be closed by such caps at one end and by the plugs at the opposite end.

In one embodiment the device comprises a spindle with the first and second threads being arranged on the spindle. For example the first and second threads may be arranged on different sections along a longitudinal axis of the spindle. The first and second threads may have generally the same outer diameter. The device further preferably comprises a first link and a second link. The first and second links are preferably engaged with the spindle. The first thread may form part of a screw connection between the first link and the spindle, and the second thread may form part of a screw connection between the second link and the spindle. Thus a rotation of the first link and the spindle relative to one another about a rotation axis (which is preferably an axis parallel to or coaxial with the longitudinal axis of the spindle) also causes the first link and the spindle to displace in a direction generally parallel to the rotation axis. This displacement may be used to move the piston for extruding the dental material.

In one embodiment the first link is arranged stationary relative to the device. This means that preferably the first link and the device do not move relative to one another in a direction generally parallel to the rotation axis when the piston is moved. The first link may for example be fixed in place in the device and additionally locked against rotation. The spindle of this embodiment may be rotatable relative to the first link about the rotation axis. Further the second link may be locked against rotation, but displaceable relative to the first link in a direction generally parallel to the rotation axis. Therefore a rotation of the spindle may cause the spindle to displace relative to the first link and further to displace relative to the second link. In this embodiment the first and second threads preferably have the same handedness, but different first and second pitches. If the first and second threads had the same pitch the displacement of the spindle would be the same relative to the first link and relative to the second link. However because according to the invention the first and second pitches of the first and second links, respectively, are different the displacements of the spindle relative to the first link and relative to the second link are also different. Therefore in this embodiment a relative displacement of the first link and the second link occurs in a direction generally parallel to the rotation axis upon rotation of the spindle.

In a preferred embodiment the device is adapted such that the spindle is drivable by a motor of the device. In particular the spindle may be connected to a motor. For example the spindle may be directly connected to a motor shaft of a motor, or the spindle may be connected to the motor via a transmission, for example a geared transmission, a belt transmission, or any other suitable transmission. The motor is preferably an electric motor, for example a DC or AC motor.

In one embodiment the device comprises first and second plungers and a link. Both, the first and second threads are preferably arranged on the first plunger. The first thread may form part of a screw connection between the first plunger and the link. Further the second thread may form part of a screw connection between the first and second plungers. The link may be arranged stationary relative to the device. The link may for example be fixed in place in the device and additionally locked against rotation. The first plunger of this embodiment is preferably rotatable relative to the first link about the rotation axis. Further the second plunger may be connected to the piston. The second plunger may be locked against rotation but may be displaceable in a direction generally parallel to the rotation axis. Therefore a rotation of the first plunger preferably causes the first plunger to displace relative to the link in a direction generally parallel to the rotation axis. Further the same rotation of the first plunger preferably causes the first plunger to displace relative to the second in the same direction. Again due to the different first and second pitches but the same handedness of the first and second threads, respectively, a relative displacement between the first plunger and the link a direction generally parallel to the rotation axis is caused, which may be used to move the piston. The device of this embodiment is preferably adapted such that the first plunger can be driven by a motor of the device. In particular the first plunger may be connected to a motor, for example directly to a motor shaft of a motor or indirectly via a transmission as mentioned above. Again the motor may be an electric motor, for example a DC or AC motor.

In a preferred embodiment the first and second threads have the same handedness, as mentioned. However in certain embodiments the first and second threads may have opposite handedness.

In one embodiment the device comprises a link, a first plunger and a second plunger. The first thread preferably forms part of a screw connection between the first plunger and the link, and the second thread preferably forms part of a screw connection between the second plunger and the link. For example the first and second threads may both be arranged on the link, and the first and second plungers may have corresponding threads for co-operating with the first and second threads. In this embodiment the first plunger is preferably arranged stationary relative to the device, for example fixed in place and locked against rotation about the rotation axis. Further the second plunger may be displaceable in a dimension parallel to the rotation axis. The second plunger may be connected to the piston. Thus the piston may be advanced or retracted by the second plunger. A rotation of the link preferably causes the link to displace relative to the first plunger in a direction parallel to the rotation axis. The same rotation of the link preferably causes the link to displace relative to the second plunger in the same direction. In this embodiment the first and second threads are outer and inner threads, respectively, and preferably have opposite handedness. Therefore preferably one of the first and second threads is a left-handed thread and the other one of the first and second threads is a right-handed thread. The first and second threads have different first and second pitches so that the rotation of the link also causes a relative movement between the first and second plungers. The device of this embodiment is further adapted such that the link can be driven by a motor of the device.

In one embodiment the piston may be movable over a first distance for extruding the dental material, and the spindle drive by rotation of the screw connections comprised therein may provide for moving the piston over a second distance which corresponds to only a part of the first distance. In such an embodiment the spindle drive as such may be movable relative to the piston in a direction generally parallel to the rotation axis. Therefore the spindle drive may provide for moving the piston over the second distance, may be moved relative to the piston, and subsequently may further move the piston over the second distance. This process may be repeated until the piston is moved over the first distance. Therefore the length of the spindle drive may be minimized. This may be advantageous for providing a relatively compact device.

In the embodiments described herein more than one part of the spindle drive may be drivable by a motor. For example in the embodiment comprising a first and a second link the first and/or the second links may be drivable in addition to the spindle. For example at least one of the first and second links may be rotated in one direction while the spindle is rotated in the other direction. Thus a rapid advancement may be achieved between the at least one link and the spindle. Such a rapid advancement may be used for retracting the piston from the dental material. Therefore the device may allow a relatively quick retraction of the piston from the material. Thus an exchange of an empty or partially empty material cartridge may be facilitated. The skilled person will recognize that the identical principle can be implemented in other embodiments described herein. For example in one embodiment the first and/or second plungers as well as the link may be drivable by a motor of the device.

DETAILED DESCRIPTION OF THE INVENTION

Figure 1:
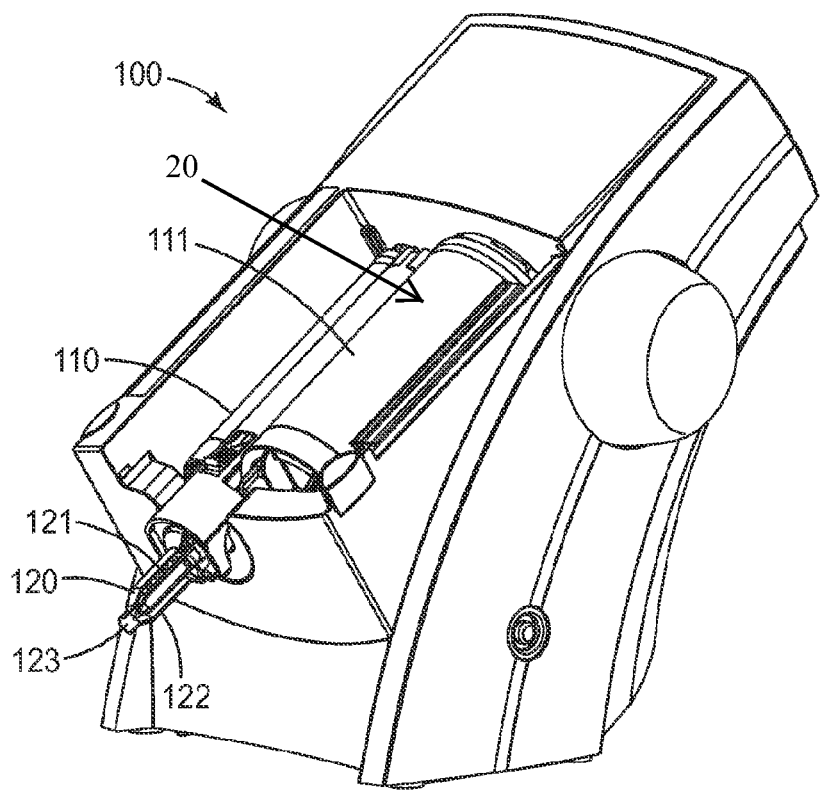
FIG. 1 is a perspective view of a device for dispensing dental material according an embodiment of the invention.

FIG. 1 shows a device 100 for mixing and dispensing dental materials. The device is motorized and therefore allows for automatic dispensation of the materials. The device 100 holds two components of a dental material in containers 110, 111. A mixer 120 for mixing the two components is attached to the device 100. The mixer 120 has a mixing chamber formed between a rotatable mixing rotor 121 and a mixer housing 122. The mixer is connected with the containers 110, 111 such that the individual components can flow into the mixing chamber. The mixture can exit through an outlet 123 of the mixer 120. The device 100 is adapted to drive the mixing rotor 121 so as to mix the components in the mixing chamber. The device 100 implements a continuous dynamic mixing process in which components can be continuously supplied into the mixing chamber and in which the mixture from the components can be dispensed continuously from the mixer. Thus the device allows preparation for variable amounts of dental materials without the need of pre-determining amounts of initial components of the mixture. The components can be advanced toward the mixer 120 by a piston (not shown) of the device 100. Both the mixer and the piston can be driven by a motor, or individual motors, in conjunction with a spindle drive 20 in the device 100.

The device shown may be used to mix and dispense a hardenable dental impression material, for example. The mixed material may be used to fill a dental tray which is then placed into a patient's mouth to take a dental impression. The mixer is attached replaceably at the device 100. Therefore when the mixed material hardens and thus blocks the mixer the used mixer may be replaced by an unused mixer for the next use of the device.

Figure 2:
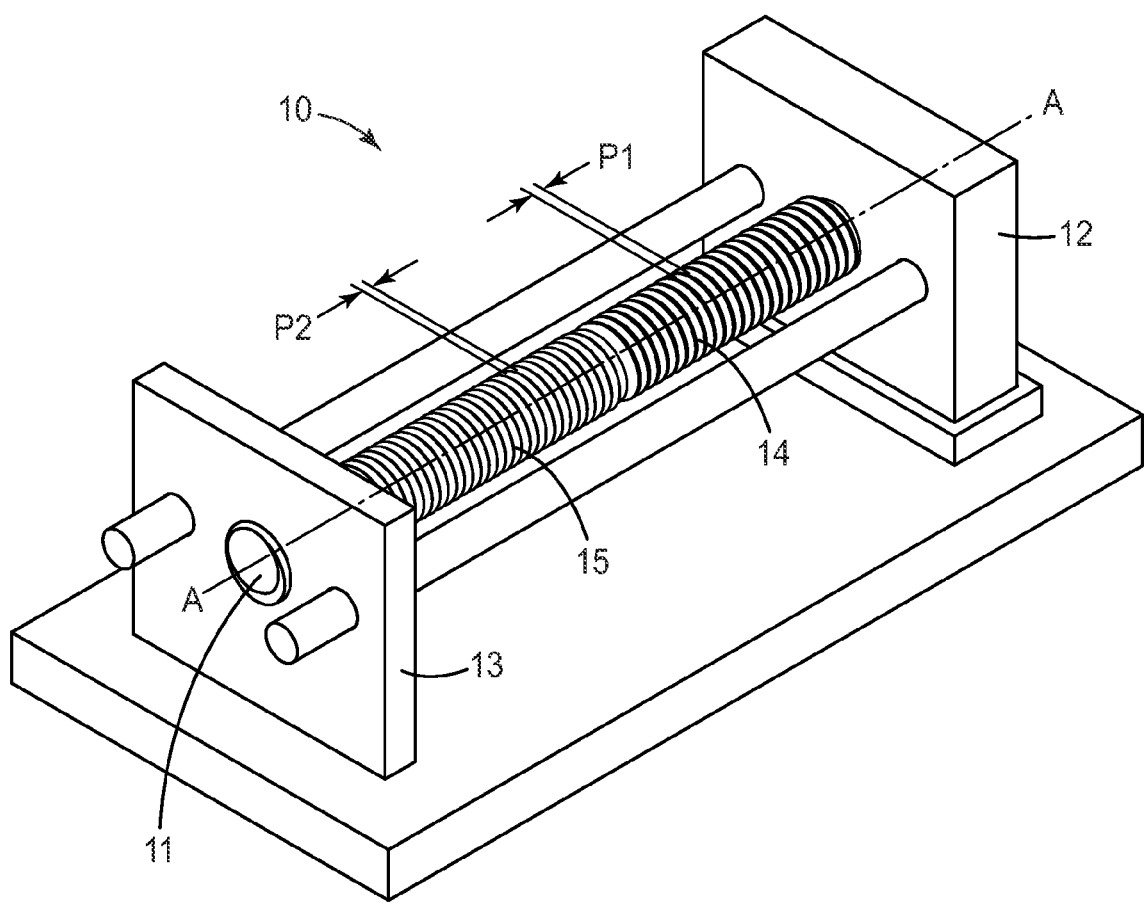
FIG. 2 is a perspective view of a spindle drive according to an embodiment of the invention.

FIG. 2 illustrates a spindle drive 10 which has a spindle 11 and first and second links 12, 13. The spindle drive 10 may be generally used to convert a rotational input motion in a linear output motion. The linear output motion may be used to move a piston for extruding dental material from a dental dispensing device (not illustrated in this Figure). The spindle 11 has a first thread 14 and a second thread 15 which are in engagement with threads of the first and second links 12, 13 respectively. Therefore the spindle drive 10 is adapted such that a rotation of the spindle 11 and the first link 12 relative to one another causes a linear displacement of the spindle 11 and the first link 12 relative to one another in a dimension along a rotation axis A. Further the spindle drive 10 is adapted such that a rotation of the spindle 11 and the second link 13 relative to one another also causes a linear displacement of the spindle 11 and the second link 13 relative to one another in a dimension along the rotation axis A. In particular the first and second threads 14, 15 (along with the respective corresponding threads of the links) have different pitches but the same handedness. In the example the first thread 14 has a first pitch P1 that is smaller than a second pitch P2 of the second thread 15. Therefore a rotation of the spindle 11 causes a displacement between the spindle 11 and the first link 12 which is larger than the displacement caused between the spindle 11 and the second link 13. The displacements of the spindle 11 and the first and second links 14, 15 relative to each other are in the same direction due to the handedness of the first and second threads being the same. Due to the different pitches a relative displacement of the first and second links 12, 13 is caused which is further explained in FIGS. 3a, 3b.

Figure 3A:
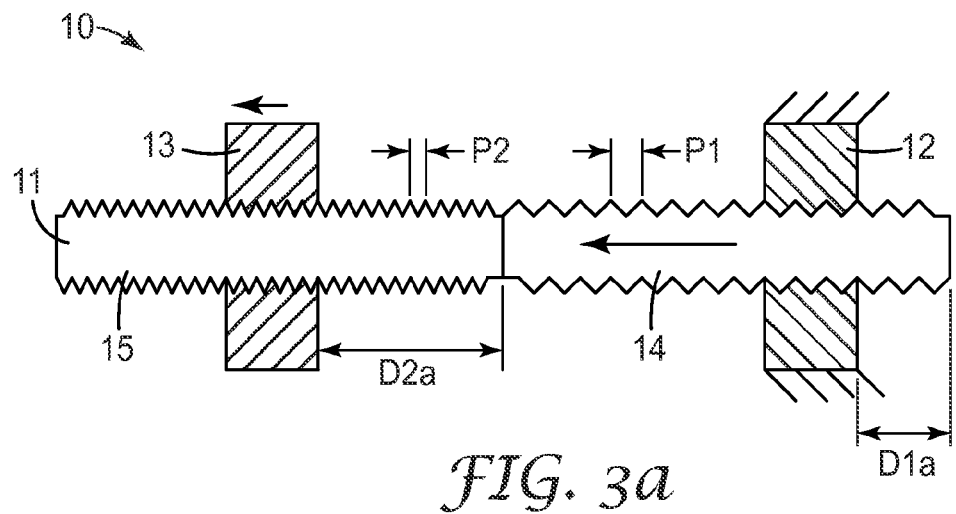
FIG. 3a, 3b are schematic views illustrating an operation of the spindle drive shown in FIG. 2.
Figure 3B:
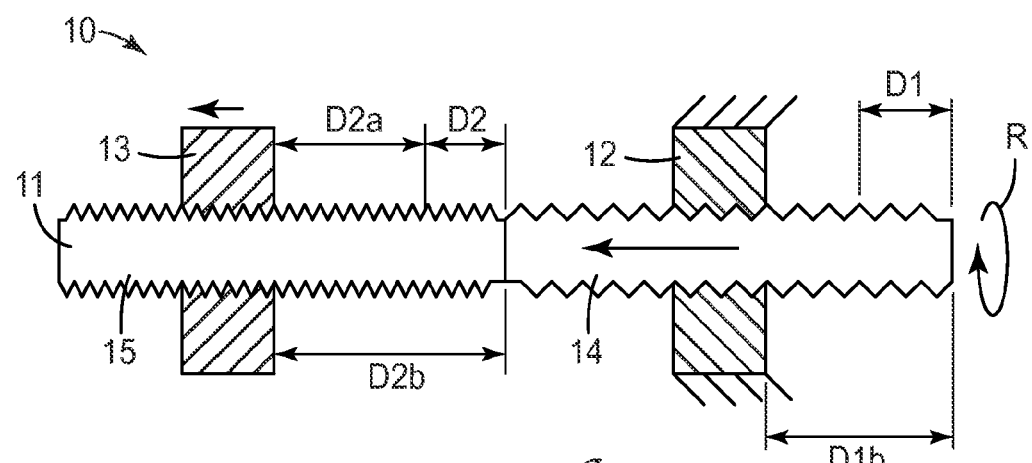

FIG. 3a and FIG. 3b show the spindle drive 10 at two different stages of operation. The figures show the spindle 11, and the first and second links 12, 13. The first link 12 is arranged stationary, for example stationary to the dispensing device (not shown) within which the spindle drive 10 may be used. The second link 13 may be connected with a piston (not shown) of the dispensing device.

FIG. 3a shows an initial operation stage of the spindle drive 10 and FIG. 3b shows the spindle drive 10 with the spindle 11 rotated by a number of rounds R about the rotation axis A relative to the initial stage. At the stage shown in FIG. 3b the spindle 11 is displaced by a first distance D1 relative to the initial stage (D1=D1b−D1a). The first distance D1 can further be calculated from the rounds R and the first pitch P1 of the first thread 14 by the formula D1=R*P1. Further the spindle 11 is displaced by a second distance D2=D2b−D2a relative to the second link 13. Again the distance D2 can also be calculated form the formula D2=R*P2. Due to the first and second pitches P1, P2 being different, the displacement D1 of the spindle 11 relative to the first link 12, and the displacement D2 of the spindle 11 relative to the second link 13, are also different. Thus a relative displacement between the first and second links 12, 13 is caused by a rotation of the spindle 11. The relative displacement between the first and second links 12, 13 can be calculated by the formula D=D1−D2 or D=R*(P1−P2). In case the difference between P1 and P2 is relatively small, the relative displacement between the two links is also relatively small even though the number of rounds R may be relatively high. Therefore the first and second pitches P1, P2 may be selected such that a high number of rounds R only causes a relatively small relative displacement between the first and second links 12, 13. The individual pitches P1 and P2 each may be relatively large (but slightly different) to provide relatively mechanically stable threads 14, 15. Therefore the spindle drive 10 may be adapted to provide a relatively slow output motion when driven at a relatively high input motion, but further (due to the stability of the threads) may be adapted to provide a relatively high force on the output motion. In particular the spindle drive may be driven by a standard motor providing a relatively high rotation speed, but may still provide a slow displacement rate at high displacement forces. Thus additional gear boxes may be saved, for example.

In one example the input motion may be about 3000 rounds per minute, and the first and second pitches may be 3 mm and 3.0075 mm, respectively so that the displacement speed is 3000 rounds per minute*(3.0075−3) mm=22.5 mm per minute.

Figure 4:
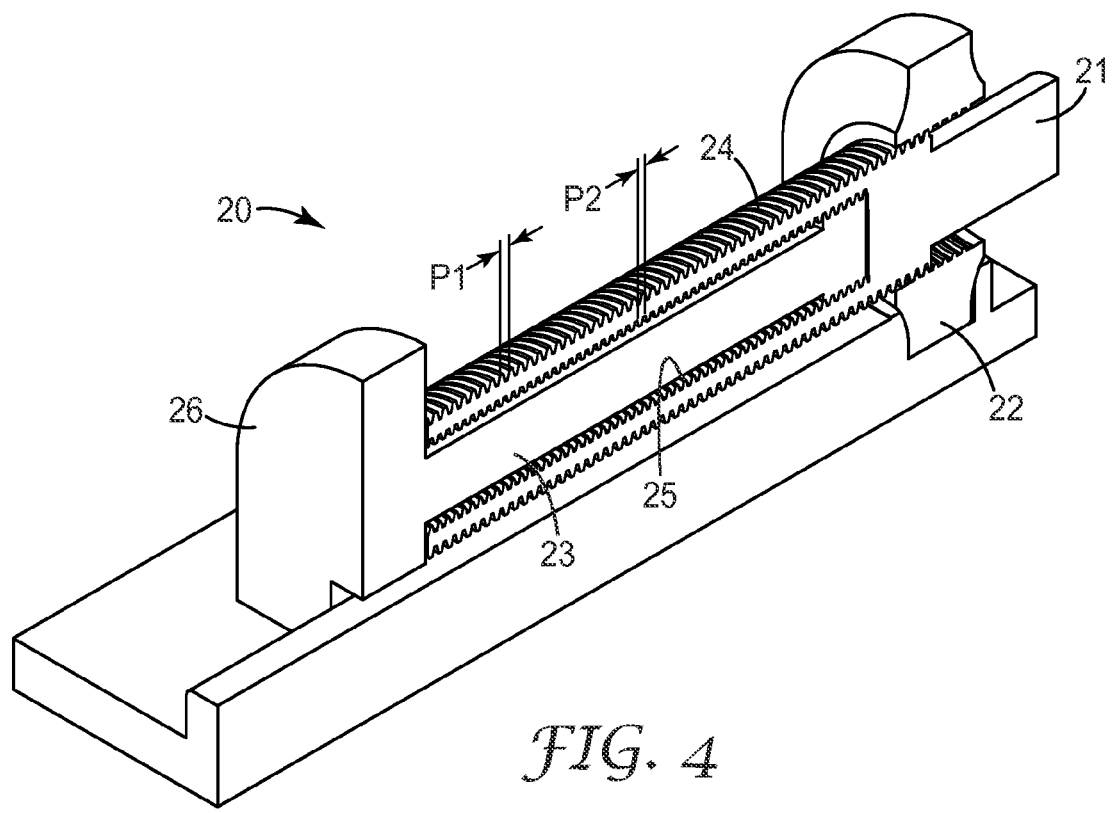
FIG. 4 is a perspective view of a spindle drive according to another embodiment of the invention.

FIG. 4 shows a spindle drive 20 which is based on the same operation principle as the examples illustrated in FIG. 2 and FIGS. 3a/3b. The spindle drive 20 has a first threaded link 22 and a first threaded spindle or plunger 21 forming a screw connection with one another. The first link 22 is arranged stationary, and the plunger 21 is displaceable (by rotation) relative to the first link 22. The plunger 21 forms a hollow spindle having an outer first thread 24 and an inner second thread 25. The spindle drive 20 further has a second plunger 23. The first and second plungers 21, 23 form a screw connection with one another of which the second thread 25 is part of. Therefore the second plunger 23 is at east partially accommodated within the first plunger 21. The second plunger 23 bears a pressure plate 26 for dispensing material from a (not shown) dispensing device. The pressure plate 26 and the link 22 are locked against rotation relative to the dispensing device, although the pressure plate 26 is linearly displaceable for dispensing material. The first and second threads 24, 25 have different first and second pitches P1, P2, respectively. Therefore a rotation of the first plunger 21 relative to the second plunger 23 and the link 22 causes the second plunger 23 and the link 22 to displace relative to one another as illustrated in FIGS. 5a, 5b.

Figure 5A:
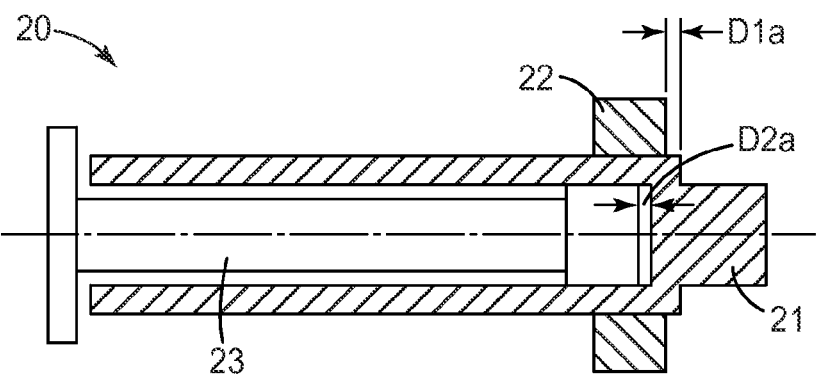
FIG. 5a, 5b are schematic views illustrating an operation of the spindle drive shown in FIG. 4.
Figure 5B:
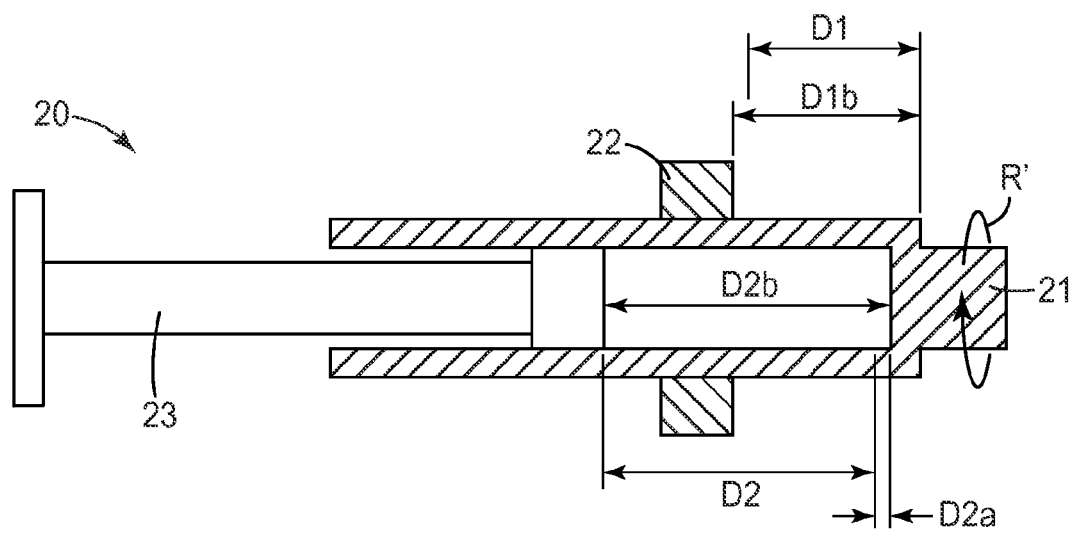

FIG. 5a shows the spindle drive 20 in an initial position, whereas FIG. 5b shows the spindle drive 20 in a position where the first plunger 21 is rotated by a number of rotations R'. A first displacement D1=D1b−D1a is present between the first plunger 21 and the link 22, and a second displacement D2=D2b−D2a is present between the first plunger 21 and the second plunger 23. As explained above the first and second displacements are different because of the first and second pitches P1, P2 (indicated in FIG. 4) being different. Again the first and second pitches P1, P2 may be selected such that a high number of rounds R' only causes a relatively small relative displacement.

Figure 6:
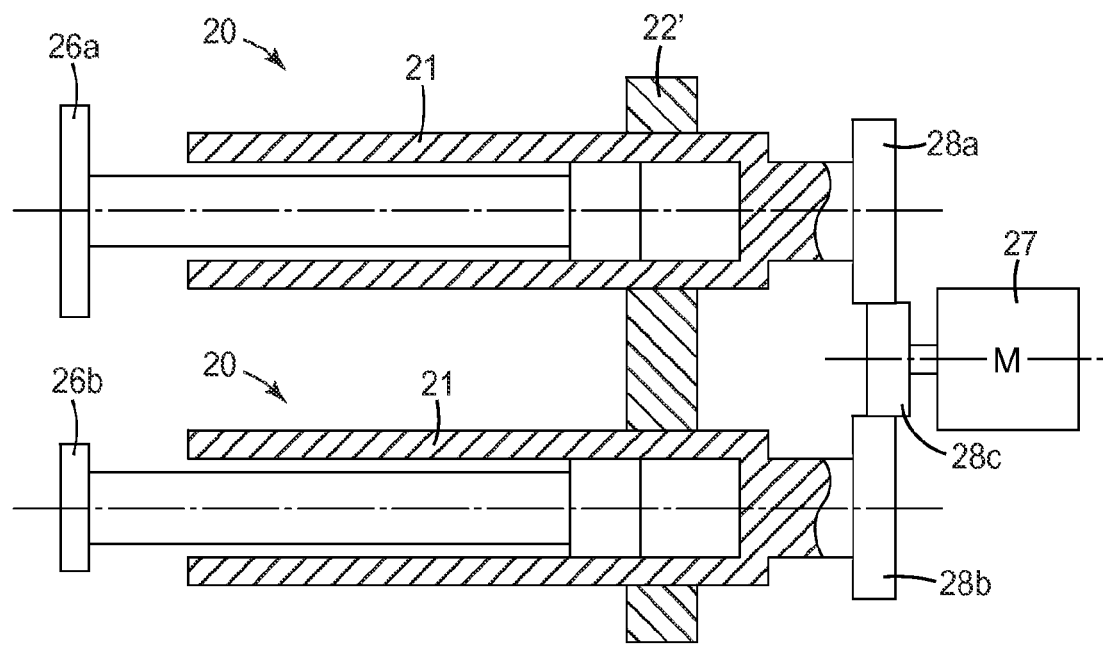
FIG. 6 is a cross-sectional view of the spindle drive shown in FIG. 4 in combination with a motor for driving the spindle drive.

FIG. 6 shows two spindle drives 20 in combination. A common link 22' is provided for co-operation with the first plungers 21 of the spindle drives 20. The skilled person will however appreciate that two links may be used likewise instead of one common link. Each of the spindle drives comprises a pressure plate 26a/26b for extruding a component of dental material from a container (not illustrated). The skilled person will recognize that one spindle drive may be used to drive two pressure plates. In the example the pressure plates have different cross-sectional areas so that the pressure plates may be loaded with different forces in operation. The use of two spindle drives may in this case provide for generally simultaneous displacement of the pressure plates because tilting of the plungers relative to the container may be prevented. Thus the configuration having two spindle drives may provide for the components to be dispensed at a generally uniform mixing ratio. The spindle drives are connected to a motor 27 of the dispensing device via gears 28a, 28b, and 28c. The motor may be an electric motor, for example a DC or an AC motor.

Figure 7:
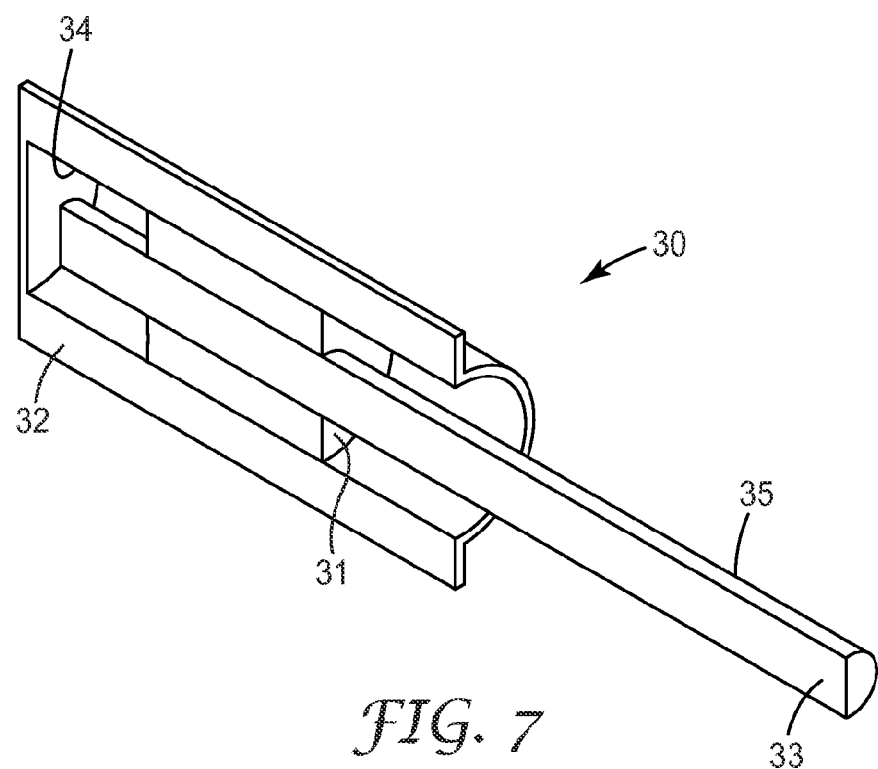
FIG. 7 is a perspective view of a spindle drive according to a further embodiment of the invention.

FIG. 7 shows a spindle drive 30 which is also based on the operation principle illustrated in the previous Figures. The spindle drive 30 has a first plunger 32 and a second plunger 33, a link 31 forming a screw connection with the first plunger 32 and a further screw connection with the second plunger 33. The spindle drive 30 has a first thread 34 and a second thread 35 which are arranged at the first and second plungers 32, 33 respectively. Therefore the first thread 34 forms part of a screw connection between the first plunger 32 and the link 31 and the second thread 35 forms part of a screw connection between the second plunger 33 and the link. The first plunger 32 may be arranged stationary and the second plunger 33 may be displaceable relative to the first plunger 32. The link 31 may be rotatable relative to the first and second plungers 32, 33. Thus a rotation of the link 31 relative to the first and second plungers 32, 33 causes a displacement of the link 31 relative to the first plunger 32 and further a displacement of the second plunger 33 relative to the link 31. In the example the first and second threads 34, 35 are of an opposing handedness. For example the first thread 34 may be left-handed, and the second thread may be right-handed. Thus for example a clockwise rotation of the link 31 causes the link 31 to displace relative to the first plunger 32 in one direction (toward the right in the Figure), but the second plunger 33 to displace relative to the link 31 in the opposite direction (toward the left in the Figure). The first and second threads 34, 35 again have different pitches P1, P2 so that the opposing displacement do not entirely compensate. Therefore a relative displacement between the first and second plungers 32, 33 is preferably caused through rotation of the link 31.

The skilled person will recognize further embodiments of the spindle drive of the invention by a combination of components having inner and outer threads which have opposing or equal handedness, and different pitches.

The invention claimed is:

1. A device for dispensing a dental material, comprising at least one compartment for receiving the dental material, and a spindle drive for moving the dental material from the compartment, the spindle drive comprising:
   a first threaded link and a first threaded hollow plunger, the first threaded hollow plunger having an outer first thread on an outer surface of the first threaded hollow plunger and an inner second thread along an inner surface of the first threaded hollow plunger, where the first threaded link and the outer first thread form a screw connection in which the first threaded link remains stationary relative to the displacement of the first threaded hollow plunger; and
   a second threaded plunger bearing a pressure plate that defines an end of the second threaded plunger, the pressure plate locked against rotation relative the first threaded link, where the second threaded plunger is at least partially accommodated within the first threaded hollow plunger to form a screw connection with one another, where the first threaded hollow plunger, rotating in a first rotational direction relative to the first threaded link, moves the pressure plate in a first linear direction relative to the first threaded link while the first threaded hollow plunger moves in a second linear direction opposite the first linear direction and where the first threaded hollow plunger rotating in a second rotational direction, opposite the first rotational direction, moves the pressure plate in the second linear direction relative to the first threaded link while the first threaded hollow plunger moves in the first linear direction opposite the second linear direction.

2. The device of claim 1, further including a motor, where the first threaded hollow plunger is drivable by the motor of the device.

3. The device of claim 1, wherein the first and second threads have the same handedness.

4. The device of claim 1, being adapted for receiving the dental material in the form of two material components, and further comprising:
- at least one cartridge containing components of the dental material
- a mixer for mixing the components; and
- a mixer shaft for receiving and driving the mixer.

* * * * *